(12) United States Patent
Pedrazzini

(10) Patent No.: US 7,004,523 B2
(45) Date of Patent: Feb. 28, 2006

(54) GRIPPING DEVICE CAPABLE TO GRIP A VIAL OR OTHER CONTAINERS WITHOUT USING MECHANICAL FINGERS OR OTHER MECHANICAL GRIPPING DEVICES

(75) Inventor: Gianandrea Pedrazzini, Segrate (IT)

(73) Assignee: E. Viridis S.A., Lugano (CH)

( * ) Notice: Subject to any disclaimer, the term of this patent is extended or adjusted under 35 U.S.C. 154(b) by 0 days.

(21) Appl. No.: 10/771,344

(22) Filed: Feb. 5, 2004

(65) Prior Publication Data
US 2004/0164571 A1 Aug. 26, 2004

Related U.S. Application Data

(60) Provisional application No. 60/446,338, filed on Feb. 6, 2003.

(51) Int. Cl.
*B66C 1/04* (2006.01)
(52) U.S. Cl. ...................... 294/65.5; 294/907
(58) Field of Classification Search ............. 294/65.5, 294/64.1, 907; 901/40
See application file for complete search history.

(56) References Cited

U.S. PATENT DOCUMENTS

| 1,739,752 | A | * | 12/1929 | Elmen ...................... 335/296 |
| 4,813,729 | A | * | 3/1989 | Speckhart .................. 294/65.5 |
| 5,348,359 | A | * | 9/1994 | Boozer ....................... 294/24 |
| 5,678,696 | A | * | 10/1997 | Goetz ........................ 209/44.2 |
| 5,845,950 | A | * | 12/1998 | Stowe et al. ................ 294/65.5 |
| 6,015,175 | A | * | 1/2000 | Carruth et al. ............. 294/65.5 |
| 6,086,125 | A | * | 7/2000 | Kovacs et al. ............. 294/65.5 |
| 6,453,543 | B1 | * | 9/2002 | Tinner et al. ................ 29/607 |
| 6,538,544 | B1 | * | 3/2003 | Hardy ....................... 335/285 |
| 6,612,633 | B1 | * | 9/2003 | Tell ........................... 294/64.1 |

* cited by examiner

*Primary Examiner*—Katherine Matecki
*Assistant Examiner*—Esther O. Okezie
(74) *Attorney, Agent, or Firm*—Jacobson Holman PLLC

(57) ABSTRACT

It is described a gripping device for vials or similar containers, comprising a tubular body attached to one end of a movable supporting vertical shaft and gripping means associated to said tubular body. Said gripping means comprise non-mechanical gripping members, able to be connected with one end of a vial or container by face-to-face soft contact.

4 Claims, 5 Drawing Sheets

GRIPPING DEVICE CAPABLE TO GRIP A VIAL OR OTHER CONTAINERS WITHOUT USING MECHANICAL FINGERS OR OTHER MECHANICAL GRIPPING DEVICES

This is a complete application claiming benefit of provisional 60/446,338 filed Feb. 6, 2003.

FIELD OF THE INVENTION

The present invention relates to a gripping device capable of gripping a vial or other containers without using mechanical fingers or other mechanical gripping devices.

BACKGROUND OF THE INVENTION

Storing biological samples (vials) presents many and complex problems especially if this is done manually at iltra-low temperatures, such as −80° C. and −190° C.

The critical aspects of the sample storing process are represented almost exclusively by the positive sample identification (ID code) and the sample handling operations based upon the "in and out motions" of the vial to and from the storage area ("deep freezer").

An automated process is then advisable but, in this case, sophisticated devices and a structured environment are required to maximize the rate "number of vials/volume of the deep freezer".

So the risks are different and serious: loss of sample integrity, loss of sample ID that is equivalent to the loss of the sample itself, dangerous handling process, biohazard.

Actually the gripping operations are made by mechanical gripping devices with all the problems mentioned before.

SUMMARY OF THE INVENTION

The object of the present invention is to provide a gripper device capable of gripping one vial at a time and bringing the operations associated with the vial handling to a very low risk level.

Accordingly, such object is achieved by a gripping device for vials or similar containers, comprising a tubular body attached to one end of a movable supporting vertical shaft and gripping means associated with said tubular body, characterized in that said gripping means comprise non-mechanical gripping members able to be connected with one end of a vial or container by face-to-face soft contact.

The advantage of such a device is that vials may be handled gently and stored side by side leaving a minimum space among them, space that would be necessary in case mechanical gripping fingers are used.

BRIEF DESCRIPTION OF THE DRAWINGS

Embodiments of the present invention will now be described by way of example only, with reference to the accompanying drawings, in which.

DETAILED DESCRIPTION OF THE PREFERRED EMBODIMENTS

Figures 1, 4:
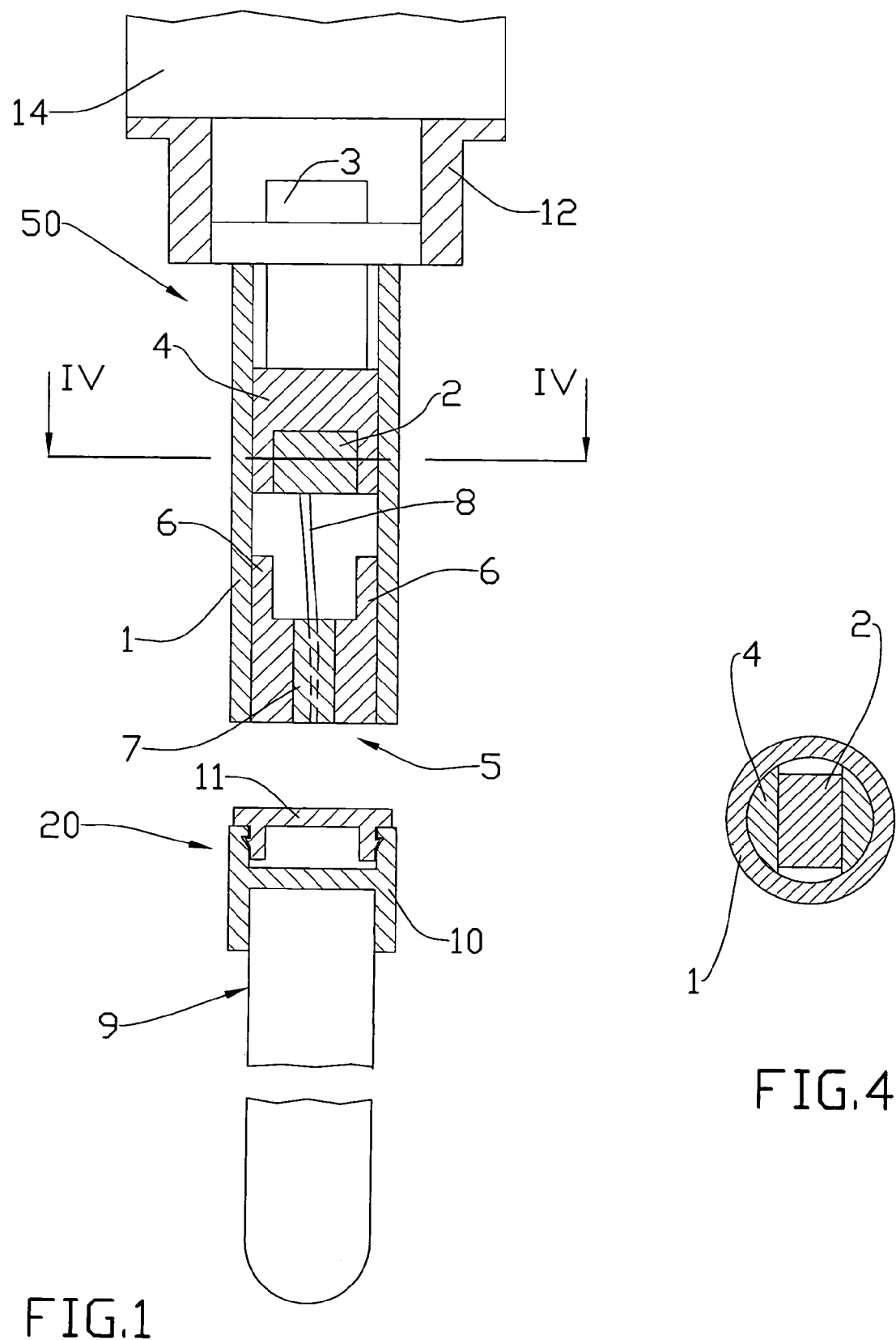
FIG. 1 is a axial-sectional view showing a first embodiment of a gripping device according to the present invention, which is provided with gripping members including a permanent magnet shown in rest position in a housing receptacle.
FIG. 4 is a cross-sectional view taken on the line IV—IV of FIG. 1.
Figure 2:
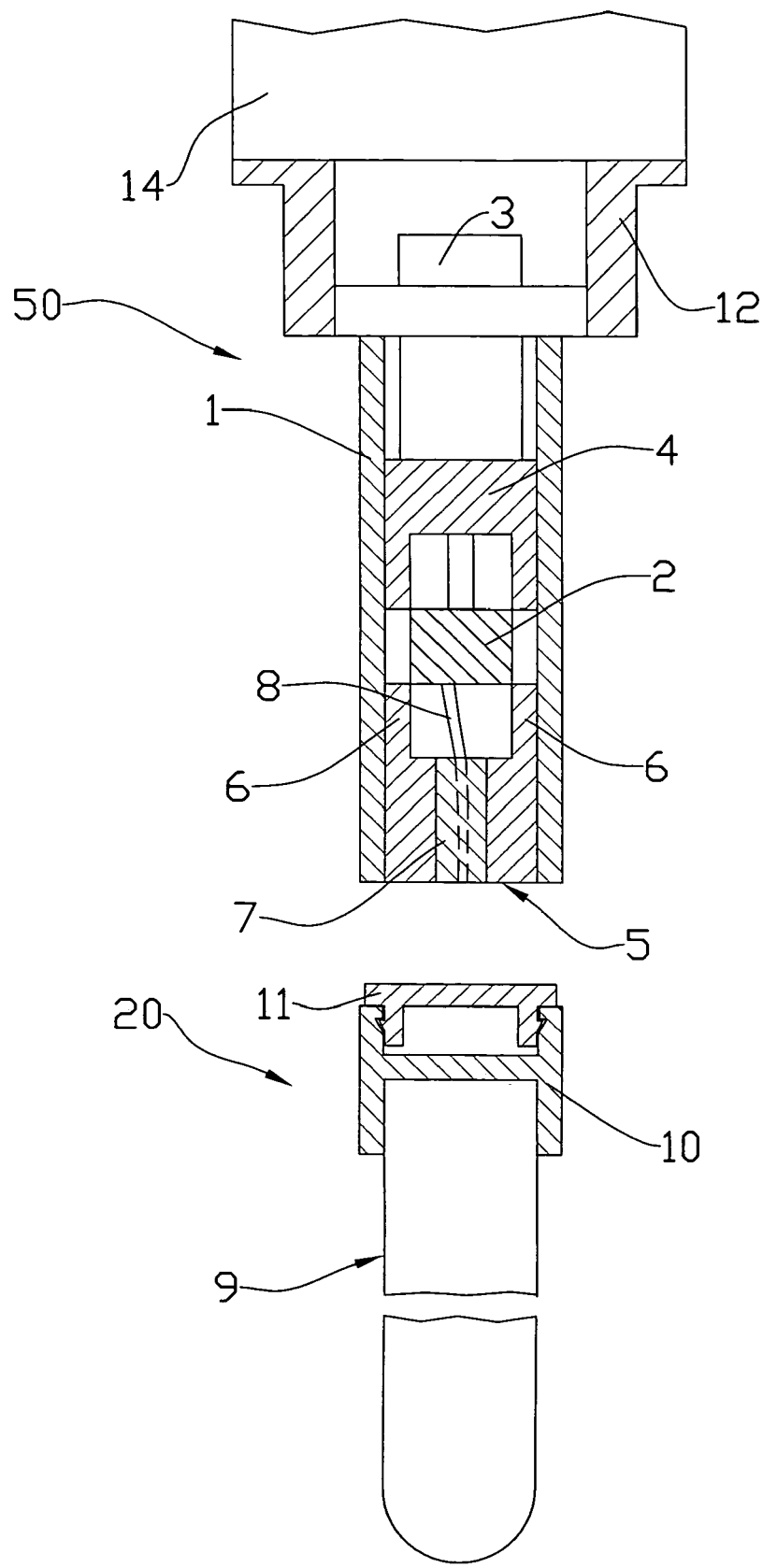
FIG. 2 is an axial-sectional view like FIG. 1 with the permanent magnet in a middle transitional position.

In FIGS 1–4 a gripping device 50 is shown comprising a cylindrical body 1 of diamagnetic material (for example stainless steel or anodized aluminum) in which a premanent magnet 2 is axially movable by means of a piston housed in a gas cylinder 3 between a rest position in a "U" shaped ARMCO ferromagnetic material iron receptacle 4 and a work position inside an ARMCO ferromagnetic material iron device 5.

"ARMCO" means any ferromagnetic material with a very low magnetic hysteresis.

The ARMCO ferromagnetic material iron device 5 consists of two legs 6 between which a plastic resin 7 is provided that incorporates an optical fiber sensor 8 for electromagnetic data transmission to an external monitoring station (not shown).

A vial 9 has on the top a vial cap 20 which comprises a vial cap 10 with an ARMCO ferromagnetic material iron top cap insert 11.

The gripping device 50 is connected with a movable supporting vertical shaft 14 by means of a supporting body 12.

When magnetic coupling is not required (rest position, FIG. 1) the permanent magnet 2 is kept at the upper position into the "U" shaped ARMCO ferromagnetic material iron receptacle 4 that is a real magnetic shield that annuls the magnetic field generated by said permanent magnet itself.

On the contrary, when a vial 9 is to be gripped, the gripping device 50 is moved toward the vial 9, in particular the bottom end of the gripping device is approached to the top of the cap 20 where the ARMCO ferromagnetic material iron insert 11 is located.

Figure 3:
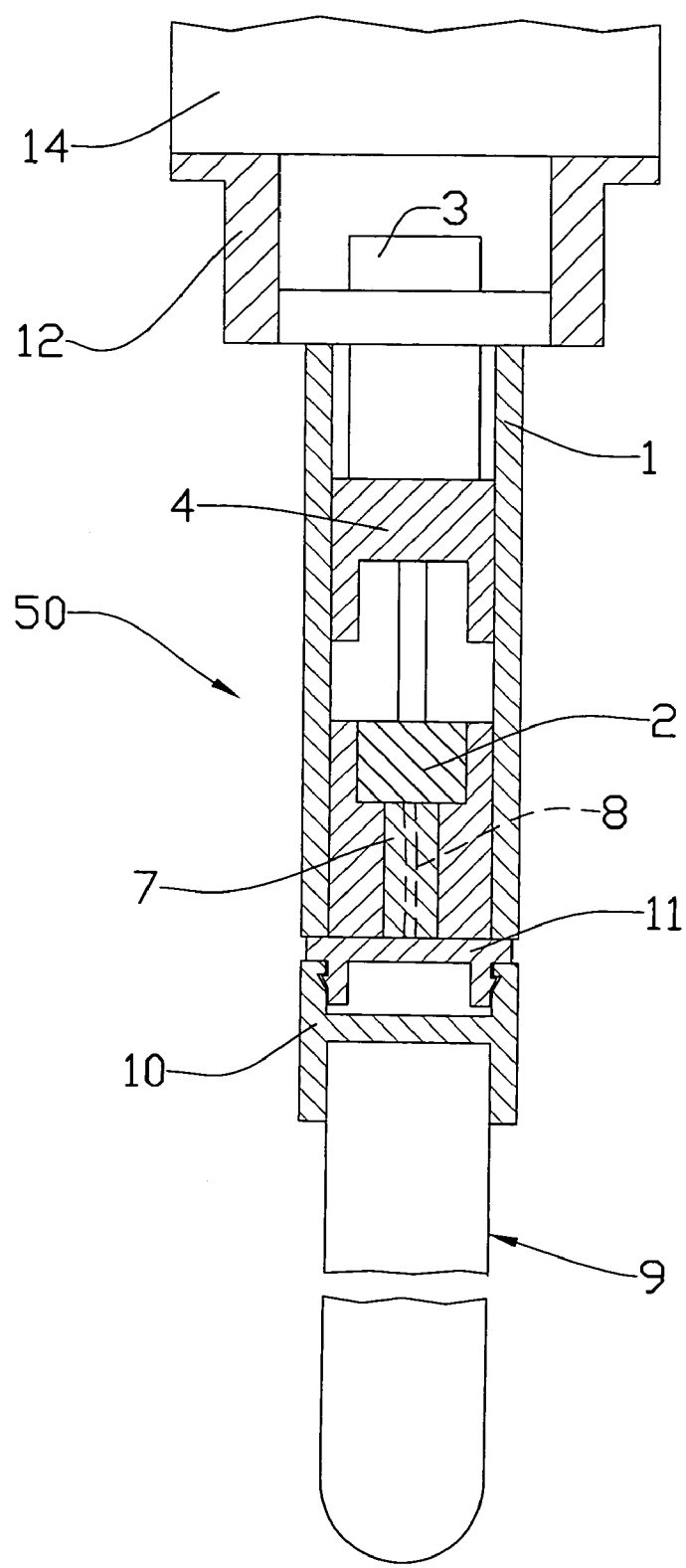
FIG. 3 is an axial-sectional view like FIGS. 1–2 with the permanent magnet in a work position.

When approaching the top of the vial 9, an optical signal, through the optical fiber 8, monitors said approach and, when the vertical shaft approach is completed, the piston of the cylinder 3 (FIG. 2) will move the permanent magnet 2 down between the two ARMCO ferromagnetic material iron legs 6 (work position, FIG. 3). Such a movement allows the magnetic field generated by the magnet 2 to be conveyed to the top 11 of the cap 20 of the vial 9 and the magnetic gripping of the vial is obtained without any mechanical engagement.

The gripping device vertical shaft 14 is then moved upwards while the optical signal monitors that the vial cap 20 keeps facing the gripping device.

The optical signal should detects if the vial cap 20 is missed during this vertical lifting and/or other following movements, so if there is evidence that the vial 9 has been lost, an error signal is generated for further investigation.

If no problems occurs, after the vial 9 has been settled in its new location, the cylinder 3 will move the permanent magnet 2 upwards again into the ARMCO ferromagnetic material iron receptacle 4 and the gripping capability is lost. The shaft may now move away leaving the vial 9 at the new location.

Also in this case the optical signal monitors that the dropping of the vial 9 into its new location has occurred correctly.

By means of the optical fiber 8 it is possible to read correctly without mistake a dot matrix code engraved on the vial by an engraving tool such as a $CO_2$ laser source equipped with appropriate optical lenses and galvanometers to drive the optical laser beam.

Figure 5:
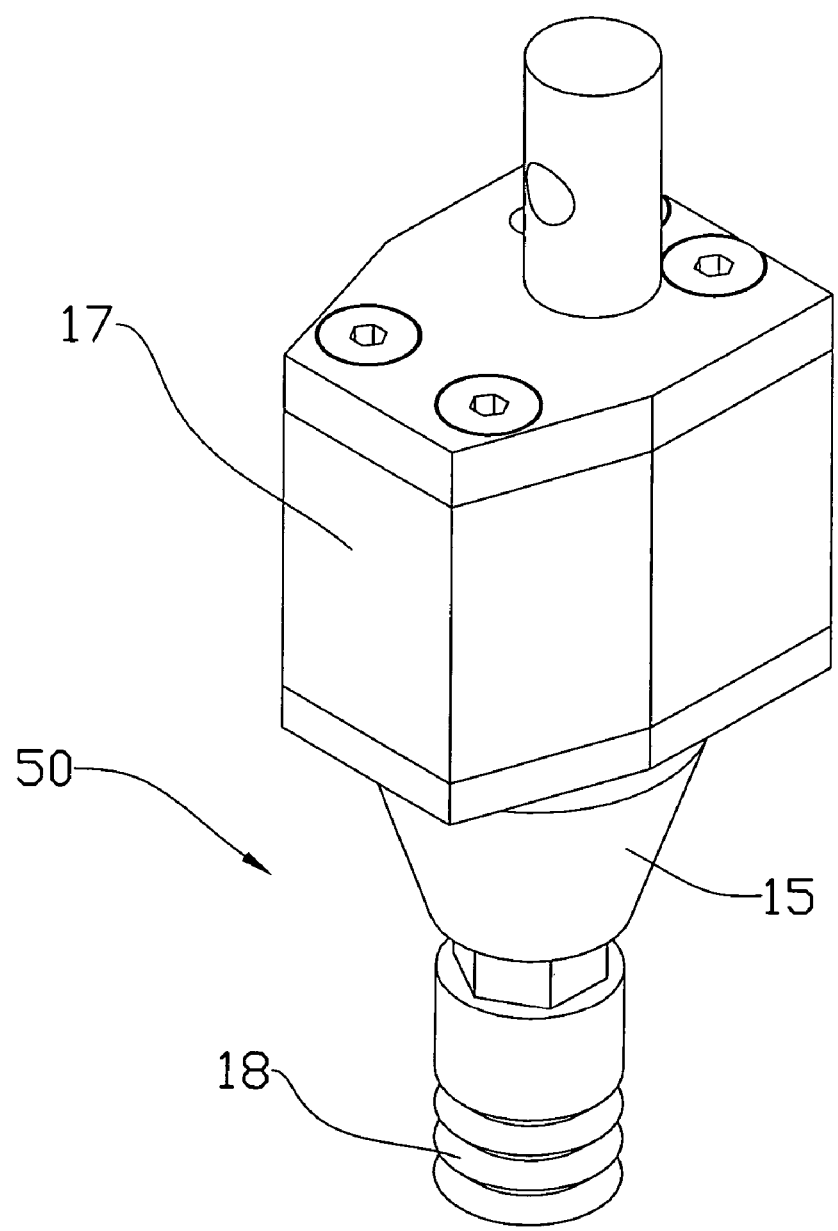
FIG. 5 is a perspective view showing another embodiment of the gripping device according to the present invention.
Figure 6:
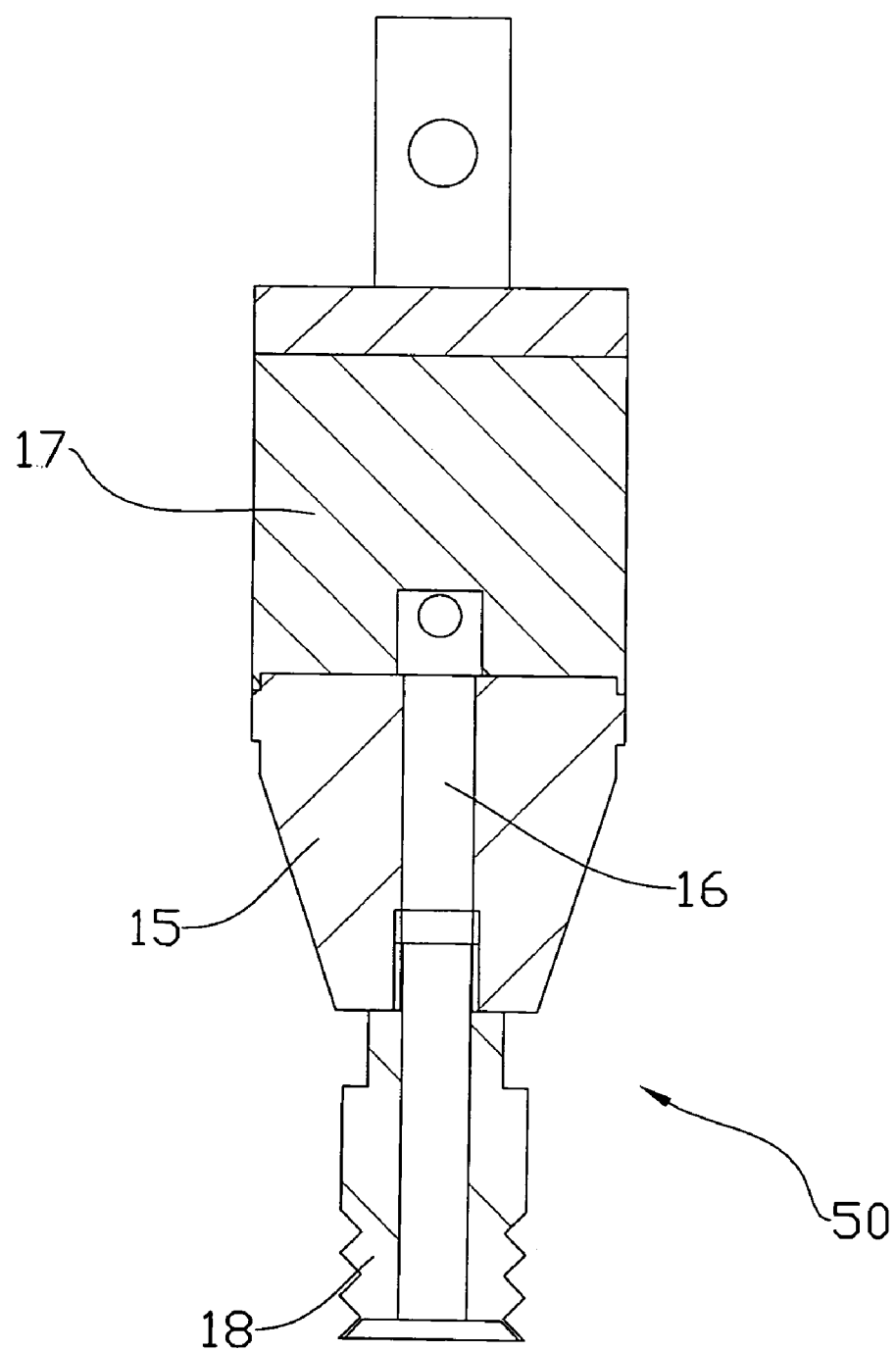
FIG. 6 is an axial-sectional view of the gripping device of FIG. 5.

An alternative to the magnetic gripping process is represented by a gripping device (second embodiment, FIGS. 5 and 6) that uses the ambient pressure in order to grip a vial 9.

Such a solution makes use of a vacuum device. In this case the top 11 of the vial cap 20 has the surface shape that matches with a suction cap 18 arranged at the lower end of a conical body 15 attached to a support body 17. A pipe 16 passing through the bodies 15 and 17 and the supporting shaft connects the suction cap 18 to a vacuum generator (not shown) located outside of the cold chamber in which the vials are located.

By generating vacuum it is possible to grip the vial 9. Such a solution is preferable when the container is a glass bulb (ampule) that has generally a conic shaped top instead of a planar cap.

An alternative to the optical fiber sensor is represented by a metal detector sensor (proximity sensor in case the top of the vial cap 20 is metallic) to monitor the coupling process between the gripping device and the vial 9 itself.

What is claimed is:

1. Gripping device for containers, said gripping device comprising a tubular body attached to one end of a movable supporting vertical shaft and gripping means associated with said tubular body, said gripping means comprise non-mechanical gripping members able to be connected with one end of a container by face-to-face soft contact, said gripping members comprise a permanent magnet axially movable inside the tubular body by a piston housed in a cylinder, the tubular body being made of a diamagnetic material, the permanent magnet being movable between a rest position in a housing receptacle and a work position inside a ferromagnetic iron device engageable by face-to-face soft contact with a ferromagnetic iron insert attached to said one end of the container.

2. Gripping device according to claim 1, wherein said ferromagnetic iron device is an iron receptacle.

3. Gripping device according to claim 1, further comprising an optical fiber optic sensor arranged inside the tubular body for electromagnetic data transmission.

4. Gripping device for a container, said gripping device comprising a gripping member provided with an external tubular body of diamagnetic material and a permanent magnet movable within the tubular body between a rest position inside a ferromagnetic iron receptacle and a work position inside a ferromagnetic iron body, and a container provided with a ferromagnetic iron insert attached to one end of the container, the permanent magnet being engageable in face-to-face contact with the ferromagnetic iron insert of the container.

* * * * *